US011291755B2

(12) United States Patent
Shidham

(10) Patent No.: US 11,291,755 B2
(45) Date of Patent: Apr. 5, 2022

(54) ARTERIOVENOUS ACCESS CATHETER WITH PROTECTABLE INLINE NEEDLE

(71) Applicant: Aadi Innovations LLC, Columbus, OH (US)

(72) Inventor: Aaditya Shidham, Columbus, OH (US)

(73) Assignee: Aadi Innovations LLC, Columbus, OH (US)

( * ) Notice: Subject to any disclaimer, the term of this patent is extended or adjusted under 35 U.S.C. 154(b) by 961 days.

(21) Appl. No.: 16/012,007

(22) Filed: Jun. 19, 2018

(65) Prior Publication Data
US 2019/0381234 A1 Dec. 19, 2019

(51) Int. Cl.
*A61M 1/36* (2006.01)
*A61M 1/14* (2006.01)
*A61M 25/06* (2006.01)

(52) U.S. Cl.
CPC ............ *A61M 1/3661* (2014.02); *A61M 1/14* (2013.01); *A61M 1/3655* (2013.01); *A61M 25/0606* (2013.01); *A61M 25/0618* (2013.01); *A61M 25/0631* (2013.01)

(58) Field of Classification Search
CPC .... A61M 1/3661; A61M 1/14; A61M 1/3655; A61M 5/32; A61M 5/321; A61M 5/3271; A61M 25/0606; A61M 25/0618; A61M 25/0631; A61B 5/153; A61B 5/150644; A61B 5/15003; A61B 5/15019; A61B 5/15074; A61B 5/150641; A61B 5/158
See application file for complete search history.

(56) References Cited

U.S. PATENT DOCUMENTS

| | | | |
|---|---|---|---|
| 4,362,156 A * | 12/1982 | Feller, Jr. .......... | A61M 25/0637 604/165.03 |
| 4,834,718 A | 5/1989 | McDonald | |
| 4,952,207 A | 8/1990 | Lemieux | |
| 5,011,475 A * | 4/1991 | Olson ................. | A61M 5/3216 604/192 |
| 5,108,376 A * | 4/1992 | Bonaldo ........... | A61M 25/0637 604/110 |
| 5,407,431 A * | 4/1995 | Botich ............... | A61M 5/3129 604/110 |
| 5,545,146 A | 8/1996 | Ishak | |

(Continued)

FOREIGN PATENT DOCUMENTS

| | | | |
|---|---|---|---|
| CN | 202822325 U | 9/2012 | |
| CN | 204017014 U | 12/2014 | |
| EP | 2204211 A2 * | 7/2010 | ........ A61M 25/0618 |

*Primary Examiner* — Philip R Wiest
(74) *Attorney, Agent, or Firm* — Standley Law Group LLP; Eric Gayan; Kenny Pung

(57) ABSTRACT

Exemplary embodiments described herein are directed to arteriovenous (AV) access catheters with inline needles that are protectable by sliding displacement of the catheter, and to methods of performing hemodialysis using said AV catheters. Extension (sliding) of the catheter portion of an exemplary device relative to a needle portion, after the needle of the needle portion has been used to access a patient fistula/graft, allows the catheter to cover the needle tip, thereby minimizing or eliminating the possibility that the needle may damage the fistula/graft. Because the needle still remains largely within the catheter, there is no risk of catheter collapse, kinking, etc., which could compromise blood flow during a hemodialysis procedure.

22 Claims, 11 Drawing Sheets

(56) References Cited

U.S. PATENT DOCUMENTS

| | | | |
|---|---|---|---|
| 5,800,400 A | 9/1998 | Hogan | |
| 5,931,815 A | 8/1999 | Liu | |
| 6,139,532 A * | 10/2000 | Howell | A61M 25/0637 |
| | | | 604/165.03 |
| 6,461,362 B1 * | 10/2002 | Halseth | A61M 25/0631 |
| | | | 600/576 |
| 6,736,798 B2 | 5/2004 | Ohkubo et al. | |
| 7,153,276 B2 | 12/2006 | Barker et al. | |
| 7,322,963 B2 | 1/2008 | Goh | |
| 7,413,560 B2 * | 8/2008 | Chong | A61M 25/0637 |
| | | | 604/158 |
| 7,556,617 B2 * | 7/2009 | Voorhees, Jr. | A61M 25/0631 |
| | | | 604/162 |
| 7,753,878 B2 * | 7/2010 | Jones | A61M 25/0637 |
| | | | 604/110 |
| 7,785,296 B2 * | 8/2010 | Muskatello | A61M 25/0612 |
| | | | 604/192 |
| 7,951,115 B2 | 5/2011 | Altman | |
| 8,591,473 B2 | 11/2013 | Jones et al. | |
| 8,597,249 B2 | 12/2013 | Woehr et al. | |
| 9,044,552 B2 | 6/2015 | Schraga | |
| 9,375,552 B2 | 6/2016 | Tremblay | |
| 2008/0319387 A1 * | 12/2008 | Amisar | A61M 25/0111 |
| | | | 604/95.04 |

* cited by examiner

ARTERIOVENOUS ACCESS CATHETER WITH PROTECTABLE INLINE NEEDLE

TECHNICAL FIELD

Exemplary embodiments described herein are directed to an arteriovenous (AV) access catheter with an inline needle that is protectable by sliding displacement of the catheter.

BACKGROUND

Worldwide there are currently about 2 million patients with End Stage Renal disease (ESRD). There were about 660,000 such patients in the United States as of 2013 according to the United States Renal Data System (USRDS). Out of those 660,000 ESRD patients, about 465,000 patients were receiving hemodialysis treatment, which is the process of removing extra fluids and toxins from the body and maintaining normal electrolyte levels by passing the patient's blood through a dialysis filter and subsequently returning the blood to the patient. Hemodialysis is typically performed in 3-4 hour sessions, three times per week.

Because hemodialysis involves extracting blood from the patient and returning the filtered blood to the patient, hemodialysis obviously requires repeated access to the arteriovenous system of the patient. A fistula or graft is commonly created in order to provide an effective vascular access point. An AV fistula is a surgically created direct connection of an artery to a vein, which becomes a permanent (but surgically reversible structure after a sufficient healing period). An AV graft, while similar to an AV fistula, employs a plastic tube to connect and artery to a vein. In either case, once the fistula/graft is ready to use, the fistula/graft provides the arteriovenous access required to remove and return a patient's blood during hemodialysis treatment. The proper function of a fistula/graft is critically important for most hemodialysis patients.

One of the most important steps in the hemodialysis process is cannulation of the fistula/graft. Two needles are typically inserted into a fistula/graft for arteriovenous access. One of the needles is used to direct blood from the patient through a connected tube to the dialysis filter of the dialysis machine, while the other needle is used to direct filtered blood from the dialysis machine through a connected tube back to the patient. Required blood flow through the needles may be on the order of 250-550 ml/min. To achieve this blood flow, the needles used are usually of large diameter (e.g., between 17 and 14 gauge).

In operation of most currently used hemodialysis needles, the skin of a patient is pierced by the tip of the dialysis needle, and the needle is further inserted until the tip also pierces the fistula/graft. Once the needle is properly placed in the fistula/graft, it is normally secured in place by taping it to the associated limb of the patient.

As should be obvious, the tip of a hemodialysis needle is sharp. Use of a typical hemodialysis needle generally results in the sharp tip of the needle floating in the fistula/graft. Consequently, any needle migration or movement of the limb of the patient in which the fistula/graft has been created, can cause the needle tip to damage the fistula/graft, such as by causing a counter puncture of the fistula/graft wall. Such a puncture can result in infiltration where blood leaks outside of the fistula/graft. Studies have reported an annual infiltration rate of about 5.2% of all hemodialysis treatments, which is a significant problem.

Because blood is typically flowing through the hemodialysis needles at rate of 250-550 ml/min, a significant amount of blood can accumulate in surrounding tissues and form a hematoma as a result of a counter puncture and associated infiltration. An infiltration can be very painful, and often times requires that the fistula/graft be allowed to heal before further use. Thus, a patient may either have to miss dialysis treatment for a period of time, or a temporary dialysis catheter may need to be placed in a central vein of the patient in order to permit continued dialysis until the fistula/graft heals. It is also possible that an infiltration can lead to permanent loss of use of the damaged fistula/graft.

It can be understood from the foregoing description that there is a heretofore unmet need for an improved device and method for providing hemodialysis arteriovenous access without fistula/graft damage. Exemplary arteriovenous catheter devices described herein satisfy this need and others.

SUMMARY

Exemplary arteriovenous catheter device embodiments described and shown herein are designed to provide hemodialysis arteriovenous access without fistula/graft damage, and may also be used to access peripheral vessels in non-dialysis patients. Generally speaking, exemplary arteriovenous catheter device embodiments include a catheter with an inline needle, where the sharp tip of the needle is protectable by the catheter during use to prevent fistula/graft or peripheral vessel damage due to limb movement or needle migration. Exemplary arteriovenous catheter device embodiments may also function to prevent needle stick injuries to persons performing hemodialysis procedures, and may allow for parking of the catheter before final engagement, which permits minor adjustments to the catheter and the needle to obtain optimum blood flow.

Certain combined hemodialysis needle and catheter devices are known. In one such known device, a needle protrudes from a catheter portion of the device and is used to pierce a patient's skin so as to facilitate insertion of the needle tip and a portion of an overlying catheter into the vasculature (e.g., fistula/graft) of the patient. Once placed in the patient's fistula/graft, the needle portion is subsequently withdrawn by retracting a plunger to leave only the catheter inserted. Retracting the needle pulls it out of the catheter and into a housing portion of the device so as to prevent needle injury to the fistula/graft during use. However, since the needle is withdrawn completely from the catheter and into housing, the catheter alone is responsible for conducting blood flow during hemodialysis treatment. Unfortunately, because the catheter is typically thin-walled plastic tubing, it is often weak, which may lead to kinking and possible partial collapse due to high blood flow rate, thereby impairing the hemodialysis procedure.

Exemplary arteriovenous catheter device embodiments described and shown herein are single use devices designed to produce arteriovenous access (i.e., fistula/graft or peripheral vessel), and to connect to a dialysis machine via elongate tubing in the case of a hemodialysis application. An exemplary arteriovenous catheter device includes an inline needle that is concentrically located within a slidable catheter portion while protruding slightly therefrom during certain times. The sharp tip of the needle may be used to pierce a patient's skin and fistula/graft or peripheral vessel, whereafter a catheter tip of the slidable catheter portion will follow the needle tip into the fistula/graft or peripheral vessel and the catheter portion may subsequently be slidably displaced to cover the needle tip during use of the device. The catheter position relative to the needle position may be releasably secured to ensure that the needle tip remains within the catheter.

The catheter of an exemplary arteriovenous catheter device is thus placed without removing the needle, thereby maintaining the catheter and needle in communication with the patient's blood without a break in the dialysis blood flow path. The needle tip is also protected by the catheter during use of the device, which prevents fistula/graft/peripheral vessel injury and infiltration in patients and needle stick injuries to health care workers and other users of the device. Further, since the needle still resides within a majority of the catheter, issues such as kinking and partial collapse of the catheter are avoided, thereby preserving blood flow. Unlike known combination needle and catheter devices, exemplary arteriovenous catheter device embodiments do not require any special training prior to use.

An exemplary arteriovenous catheter device may include a needle portion having a needle that extends from a needle hub, and a catheter portion that is supported on the needle portion and includes a catheter that extends from a catheter hub. The needle may extend concentrically within the catheter such that a sharp tip of the needle protrudes from an open end of the catheter when the catheter portion is in a retracted position. The catheter portion is slidable relative to the needle portion, such that the catheter may be linearly displaced to cover the needle tip. An exemplary arteriovenous catheter device may also include a body portion that is supported on the needle portion. The body portion may include a gripping structure that facilitates handling and use of the device, and may be provided as extending wings or in other forms that facilitate removable attachment of the device to a patient during use.

In one exemplary arteriovenous catheter device, the position of the catheter portion relative to the needle portion of the device may be maintained by a retention mechanism in the form of a detent element on the catheter hub and an associated annular groove on the needle hub, or vice versa.

In another exemplary arteriovenous catheter device, the position of the catheter portion relative to the needle portion of the device may be maintained by a retention mechanism in the form of a bolt that extends from the needle hub through a detent groove in the catheter hub.

In another exemplary arteriovenous catheter device, the position of the catheter portion relative to the needle portion of the device may be maintained by a retention mechanism in the form of a tab that extends from the needle hub through a detent groove in the catheter hub.

In another exemplary arteriovenous catheter device, the position of the catheter portion relative to the needle portion of the device may be maintained by a retention mechanism in the form of a pin or bolt that extends from the needle hub through a curved cam slot in the catheter hub. The cam slot may allow for parking of the catheter portion in an extended position before final engagement with a patient.

In at least one exemplary arteriovenous catheter device, sealing material may be located between the needle and the catheter to prevent the leakage of blood from the device during use.

In at least one exemplary arteriovenous catheter device, the needle and catheter portion of the device may be enclosed within a safety cap when not in use.

In at least one exemplary arteriovenous catheter device, the catheter hub and needle hub may be manufactured from a transparent or semi-transparent material to permit viewing of the flow of blood passing through the device during use.

Other aspects and features of the inventive concept will become apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and.

DETAILED DESCRIPTION OF THE EXEMPLARY EMBODIMENTS

Figure 1A:
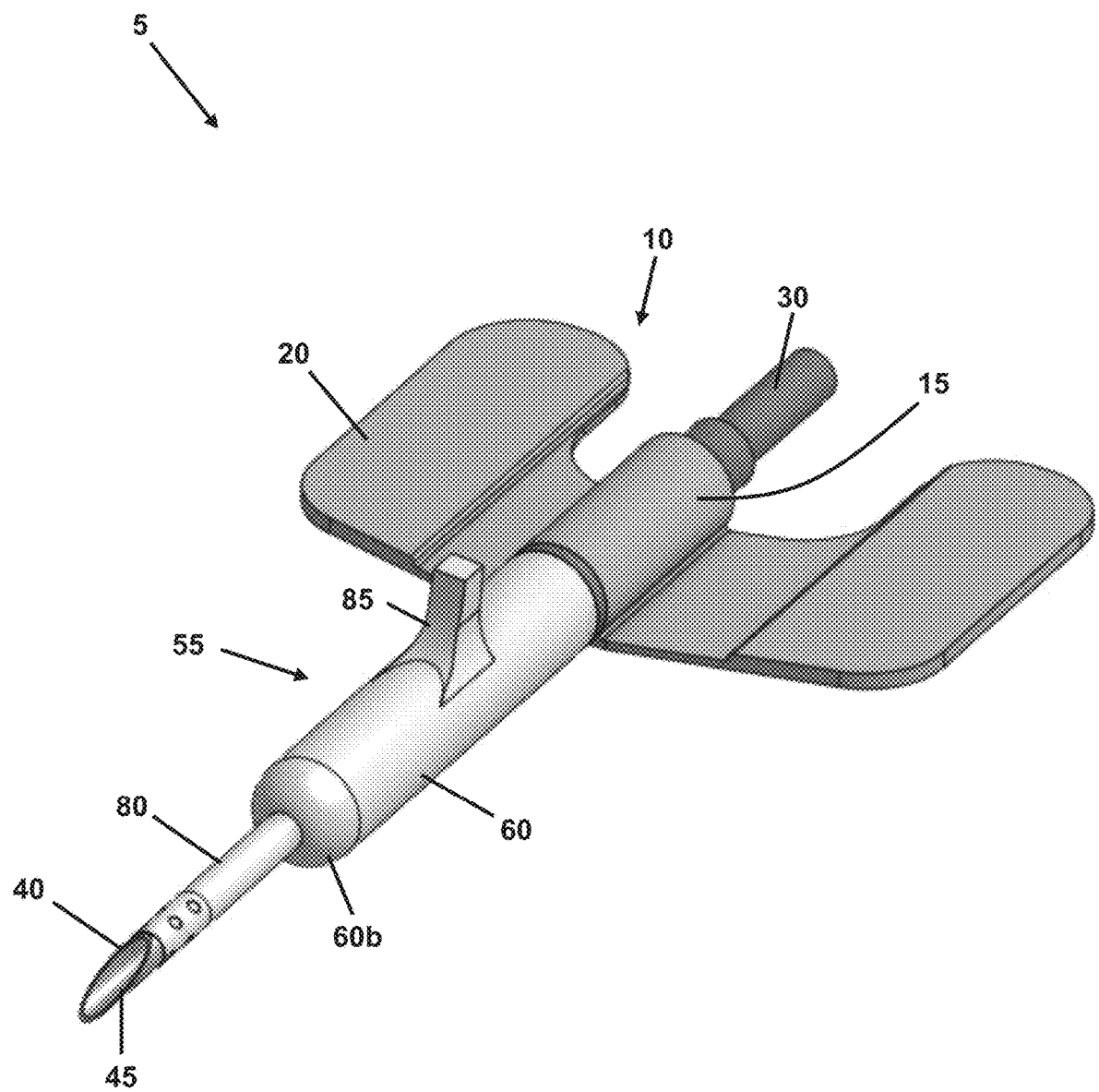
FIG. 1A is a top perspective view of one exemplary embodiment of a catheter device according to the general inventive concept, with a catheter portion thereof in a retracted position to expose a needle tip.
Figure 1B:
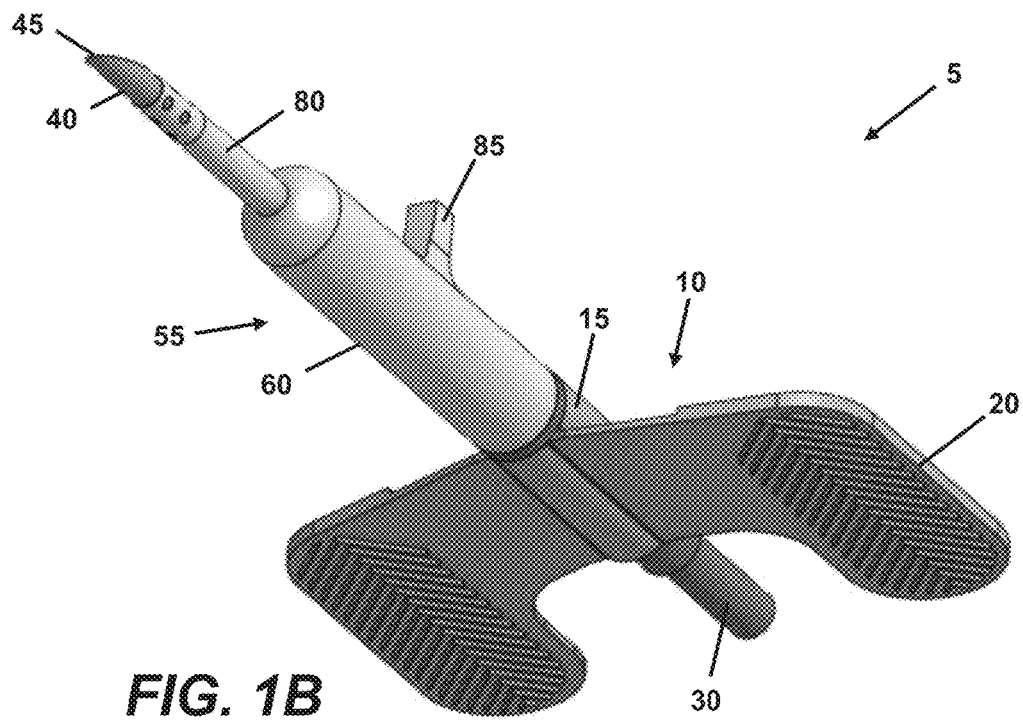
FIG. 1B is a bottom perspective view of the catheter device of FIG. 1A.
Figure 1C:
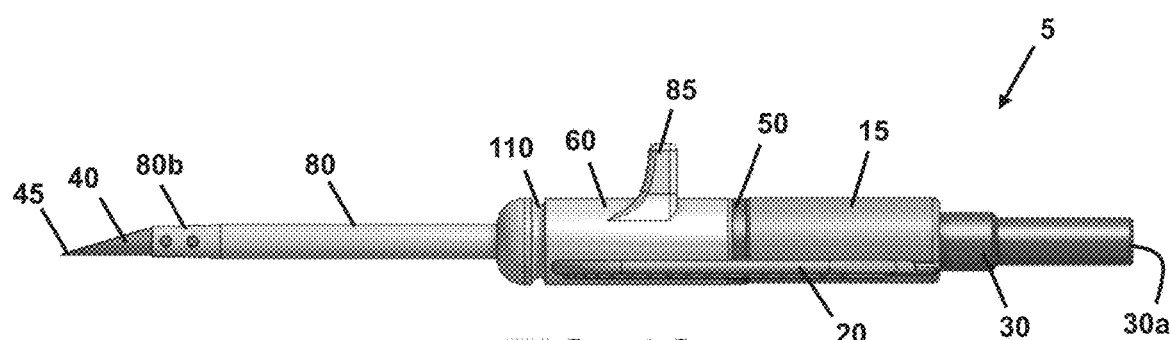
FIG. 1C is a side view of the catheter device of FIG. 1A.

One exemplary embodiment of an arteriovenous catheter device 5 is illustrated in FIGS. 1A-2D. As may be observed, the device 5 includes a needle portion 25 on which is supported a body 10 and a catheter portion 55. The body 10 includes a central mounting sleeve 15 and a pair of wing-like gripping portions 20 that extend substantially laterally outward from opposite sides of the central mounting sleeve. While the overall body 10 may be of various shapes, in this exemplary embodiment the gripping portions 20 of the body are shaped as shown to facilitate gripping and manipulation of the device 10 by a user and taping of the device to a limb of a patient after fistula/graft access. Similarly, the central mounting sleeve 15 is cylindrical and hollow in the exemplary embodiment so as to slide over a correspondingly-shaped hub of a needle portion (see below), the mounting sleeve may be of other shapes as needed to cooperate with a given needle hub. The body 10 may be constructed from various different materials, with plastic (e.g., fluoroplastic) being a particularly good material.

It also may be observed that the catheter device 5 includes a needle portion 25 and a catheter portion 55. The needle portion 25 includes an elongate needle hub 30 having a proximal end 30a and a distal end 30b. An axial bore 35 passes through the needle hub to provide, among other things, a pathway for blood flow during a hemodialysis procedure. To that end, tubing (not shown) may be coupled to the proximal end 30a of the needle hub for connecting the catheter device 5 to a hemodialysis machine, as would be understood by one of skill in the art.

A needle 40 of the needle portion 25 has a proximal end 40a thereof inserted sufficiently far into the bore 35 in the distal end 30b of the needle hub 30 to securely retain the needle. The proximal end 40a of the needle 40 may be retained in the needle hub 30 by a press fit or a similar interaction between the components. Alternatively, or in conjunction with such other techniques, an adhesive or other affixation mechanism may be used to further secure the needle 40 in the needle hub 30. A distal, free end 40b, of the needle is provided with a sharp point 45 for the purpose of piercing the skin of a patient and subsequently accessing the patient's fistula/graft. The specific needle gauge, needle construction, etc., may vary in keeping with accepted practices understood in the art.

The inside diameter of the central mounting sleeve 15 of the body 10 is dimensioned to pass over a portion of the needle hub 30. As shown, the needle hub 30 may include a protruding collar 50 or similar element that is designed and located to abut a distal face of the central mounting sleeve 15 and to thereby act as a stop for the body 10 when the body is properly installed on the needle hub 30. The collar may also act as a rear (retraction) stop for the catheter portion 55, as is described in more detail below.

The central mounting sleeve 15 of the body 10 may be retained on the needle hub 30 of the needle portion 25 by any of the same techniques mentioned above relative to securing the needle 40 in the bore 35 of the needle hub. Other techniques known to those of skill in the art may also be employed. Threaded engagement of the central mounting sleeve 15 and the needle hub 30 is also possible.

Figure 1D:
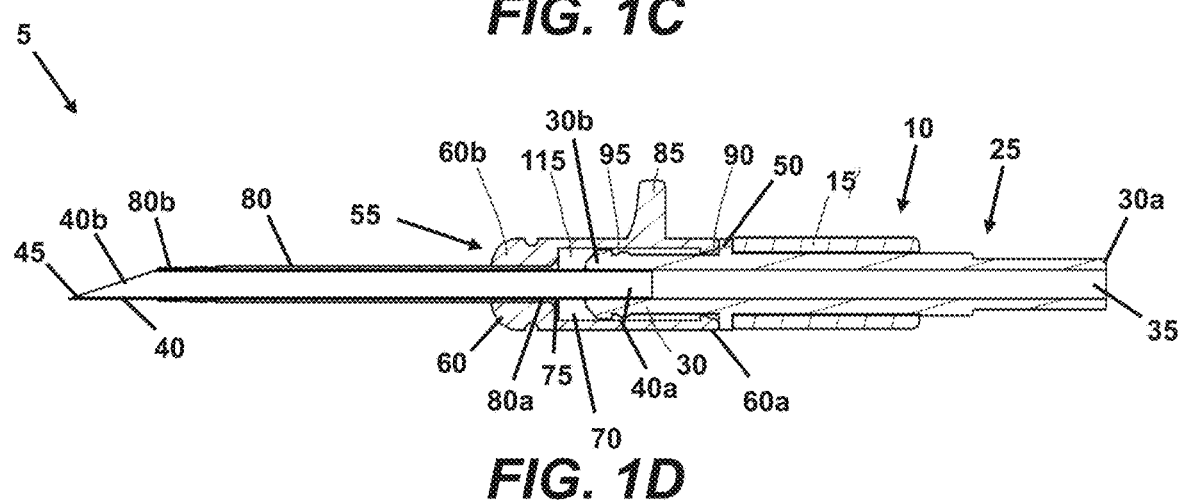
FIG. 1D is a cross-sectional view of the catheter device of FIG. 1O.

As shown particularly clearly in the section view of FIG. 1D, the collar 50 is located such that some length of the needle hub 30 extends distally therefrom. As is described below, this distally-extending portion of the needle hub 30 of this exemplary catheter device 5 is designed to retain and act as a guide for sliding movement of the catheter portion 55 of the device.

In similar fashion to the needle portion 25, the catheter portion 55 includes a catheter hub 60 with proximal and distal ends 60a, 60b. The size and shape of the catheter hub 60 is selected so that the catheter hub will cooperate with the needle hub 30. More specifically, the catheter hub 60 is of substantially cylindrical shape, and includes a first central bore 70 at the proximal end 60a that is dimensioned to permit the catheter hub to slide over the portion of the needle hub 30 that extends distally of the collar 50. This arrangement allows the catheter portion 55 of the catheter device 5 to be supported on the needle portion 25 and to slide linearly relative to the needle hub 30 (and the body 10). A second central bore 75 extends inward from the distal end 60b of the catheter hub 60 and opens into the proximally-located needle hub receiving bore 70.

The catheter portion 55 further includes a hollow catheter 80 that extends longitudinally outward from the distal end 60b of the catheter hub 60. In this exemplary embodiment, the catheter 80 has an open proximal end 80a that is inserted sufficiently far into the second bore 75 in the catheter hub 60 to securely retain the catheter. The proximal end 80a of the catheter 80 may be retained in the catheter hub 60 by any of the needle retention techniques mentioned above or by any other acceptable technique known to one of skill in the art. In other embodiments, the catheter 80 may be an integrally molded part of the catheter hub 60. A distal, free open end 80b, of the catheter 80 may be tapered and/or may include any other features that may facilitate entry of the free end of the catheter into the fistula/graft of the patient subsequent to initial access by the needle 40 and/or may facilitate blood flow during a hemodialysis procedure.

The inside diameter of the catheter is preferably similar in dimension to the outside diameter of the needle 40 so as to produce a close tolerance but sliding fit between the catheter 80 and the needle 40 when the catheter hub 60 is installed over the needle hub 30. Nonetheless, a seal 115 may be placed at or near the entry point of the second bore 75 into the first bore 70 to prevent possible blood leakage between the needle 40 and the catheter 80 during use of the catheter device 5. As with the needle 40, the specific construction of the catheter 80 may otherwise vary in keeping with accepted practices understood in the art. For example, the catheter may be constructed from a fluoroplastic material.

From the foregoing description and corresponding FIGS. 1A-2D, it should be understood that when the body 10 and catheter portion 55 are properly assembled to the needle portion 25, as explained above, the needle hub 30 is substantially concentrically located within the catheter hub 60, the needle 40 is substantially concentrically located within the catheter 80, and the catheter hub 60 and attached catheter 80 are together linearly slidable relative to the needle hub 30 and the attached needle 40. As shown in the drawing figures, a gripping element 85 or similar feature may be provided on the catheter hub 60 to facilitate sliding of the catheter portion 55 by a user of the device 5.

FIGS. 1A-1D show the catheter portion 55 in a retracted position, which results in the needle tip 45 and perhaps some additional length of the needle 40 protruding from the open distal end 80b of the catheter. This is the proper position in which the catheter portion 55 should reside during initial piercing of the patient's skin and accessing of the underlying fistula/graft using the needle 40 of the device 10.

With the tip of the needle 40 and the catheter 80 residing in the patient's fistula/graft, the catheter portion 55 may then be placed in an extended position (see FIGS. 2A-2D) by sliding the catheter portion linearly and in a distal direction along the needle hub 30 such that the sharp tip 45 of the needle becomes covered by the distal end 80b of the catheter 80. A distal catheter hub hard stop or a similar mechanism (see below) may be used to ensure proper linear positioning and possibly position retention of the catheter portion. With the needle 40 and the catheter 80 properly located in the fistula/graft of the patient, the catheter device 5 may be secured against movement, such as but not limited to by taping the gripping portions 20 of the body 10 to the limb of the patient.

As should be readily obvious to one of skill in the art, placing the catheter 80 of the exemplary catheter device 5 into the fistula/graft and over the needle tip 45 as described above serves to prevent the needle tip from damaging the fistula/graft and also, therefore, prevents infiltration and related hematoma problems. And unlike known devices, the needle 40 of the exemplary device 5 remains largely within the catheter 80 during a hemodialysis procedure, thereby substantially eliminating any chance that the catheter may collapse, kink, etc., and interfere with blood flow or cause damage on its own.

As described above, the catheter portion 55 has a retracted position where the catheter 80 is kept from interfering with use of the needle to initially access the fistula/graft of a patient. Likewise, the catheter portion 55 also has an extended position where the open distal end 80*b* of the catheter 80 will extend at least equal with if not beyond the tip 45 of the needle and into the fistula/graft currently accessed by the needle. Consequently, it is preferable to provide a mechanism by which it can be ensured that the catheter portion 55 is properly in the retracted position or the extended position, and by which either position can be maintained once selected.

In the case of the exemplary catheter device 5 of FIGS. 1A-2D, position retention is provided by a detent mechanism formed through interaction of certain elements of the catheter hub and the needle hub. This relationship may be reversed in other embodiments.

Figure 2A:
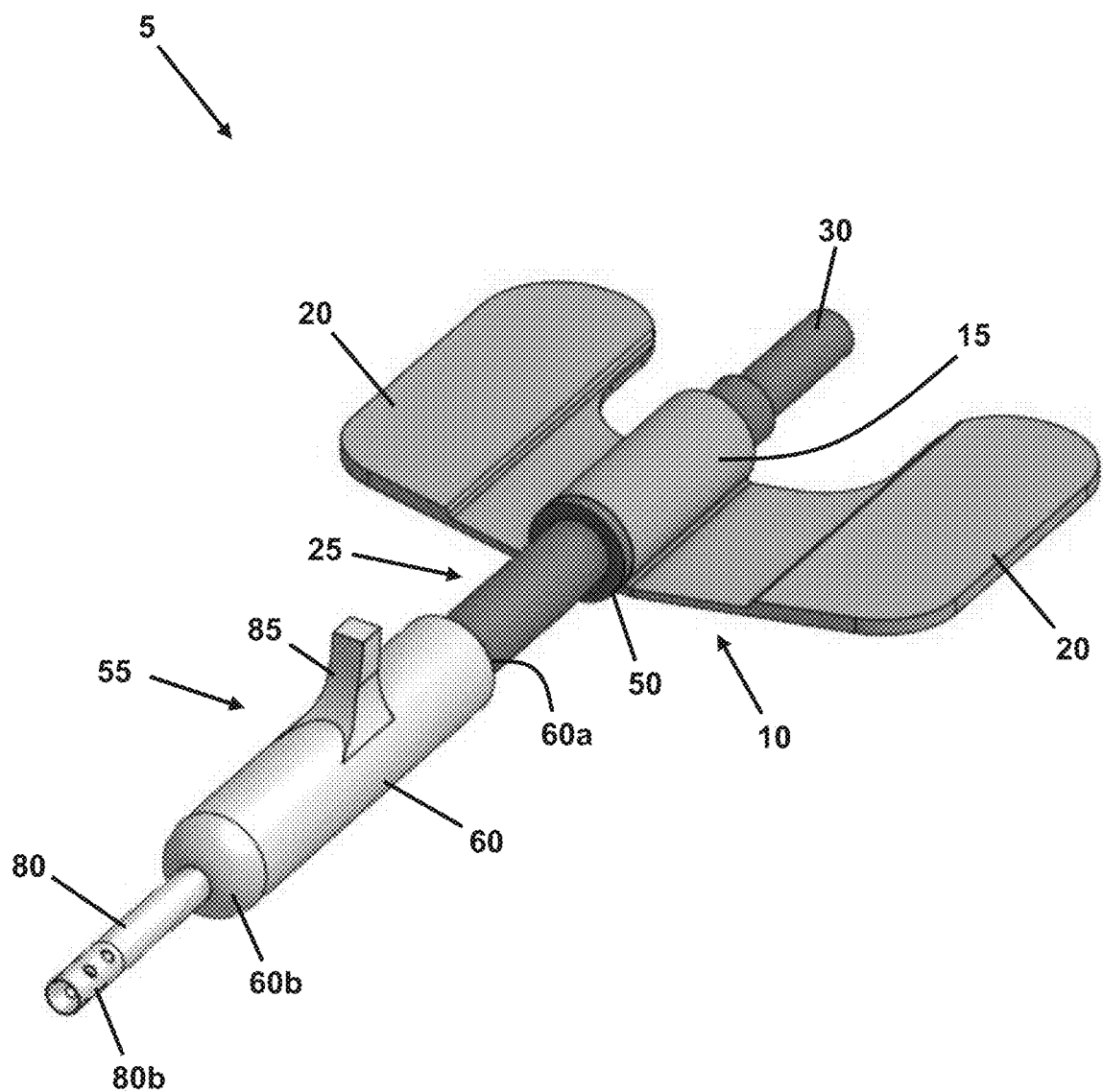
FIG. 2A is a top perspective view of the catheter device of FIG. 1A, with the catheter portion thereof in an extended position to cover the needle tip.
Figure 2B:
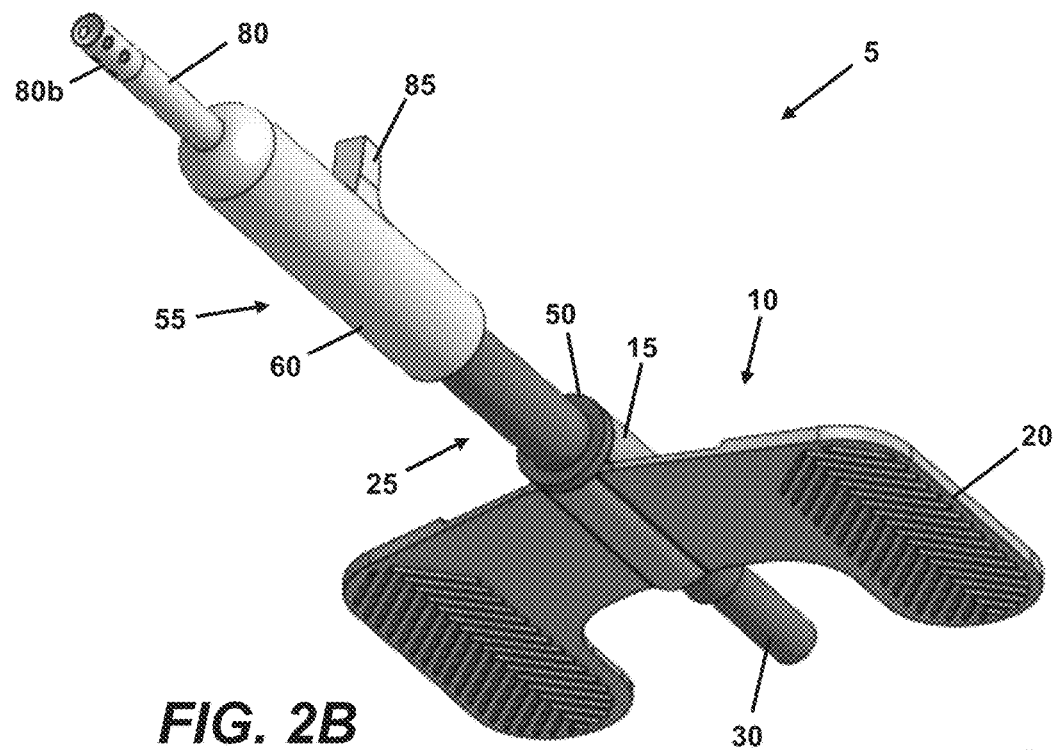
FIG. 2B is a bottom perspective view of the catheter device of FIG. 2A.
Figure 2C:
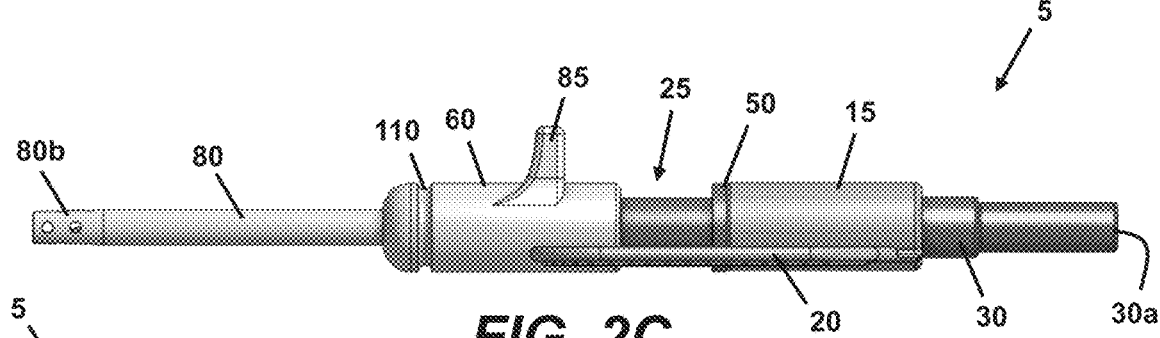
FIG. 2C is a side view of the catheter device of FIG. 2A.
Figure 2D:
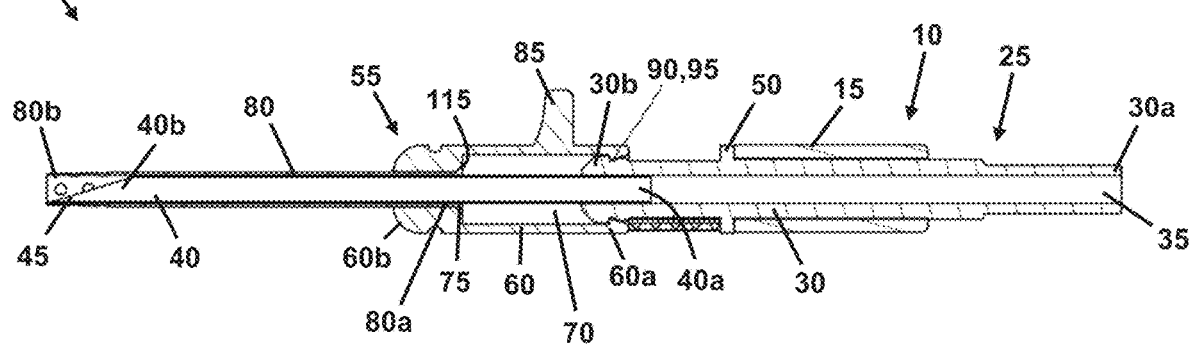
FIG. 2D is a cross-sectional view of the catheter device of FIG. 2C.

Referring to the sectional views of FIGS. 1D and 2D, it may be more specifically understood that abutting contact between the proximal end 60*a* of the catheter hub 60 and the distal side of the collar 50 of the needle hub 30 will act as a hard stop that can be used to set the proper retracted position of the catheter portion 55. It may also be observed that the exemplary catheter hub 60 of the exemplary catheter device 5 includes an inwardly-directed annular projection 90 at its proximal end 60*a*. The annular projection 90 may have a hook shape as shown, but other shapes are also possible. As explained further below, the annular projection 90 essentially acts as the lever element of the detent mechanism.

It may also be observed in FIGS. 1A and 2D that the needle hub 30 of the exemplary needle portion 25 is provided with an annular groove 95 near the distal end 30*b* thereof. The annular groove 95 essentially acts as the pawl element of the detent mechanism. As shown in FIG. 2D, when the catheter portion 55 is placed in the extended position, the annular projection 90 of the catheter hub 60 becomes releasably engaged with the annular groove 95 in the needle hub 30, thereby limiting the amount of possible linear movement and setting and retaining the extended position of the catheter portion 55, absent an overcoming displacement force provided by the user. Optionally, a second annular groove (not shown) may be similarly placed in the needle hub 30 in the area of the collar 50 to engage with the annular projection 90 of the catheter hub 60 and to releasably retain the catheter portion 55 in its retracted position absent an overcoming displacement force provided by the user.

Figure 3A:
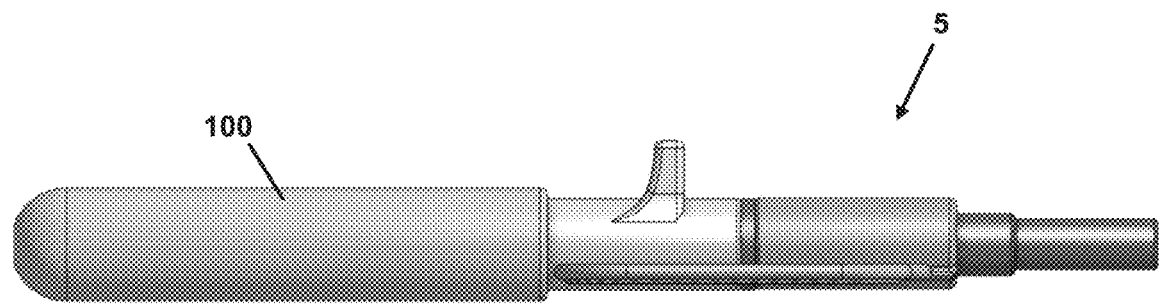
FIG. 3A depicts the catheter device of FIG. 1O with a protective cap.
Figure 3B:
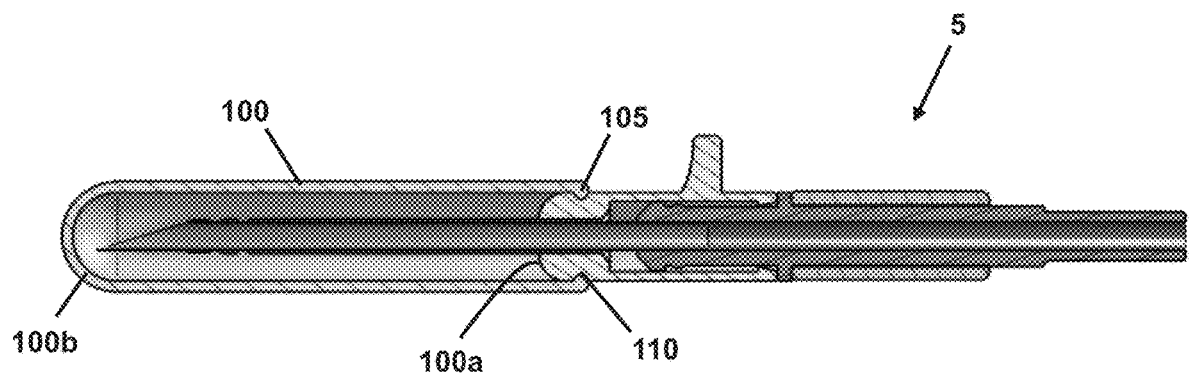
FIG. 3B depicts the catheter device of FIG. 3A with a section view of the protective cap.

To guard against inadvertent contact with the sharp tip 45 of the needle 40, a protective device may be associated with the needle. As illustrated in FIGS. 3A-3B, a cap 100 having an open proximal end 100*a* and a closed distal end 100*b* may be provided in this exemplary catheter device embodiment to enclose the needle 40 and catheter and to protect users from accidental needle sticks. When such a cap is provided, the cap may vary in shape and size. Such a cap may also be removably retained on the catheter device in different ways. In this example, the open end of the cap is provided with an inwardly-projecting retention ridge 105 that is located and configured to engage a corresponding annular cap retention groove 110 (see e.g., FIG. 10) provided in the catheter hub 60 near the distal end 60*b* thereof. Engagement of the retention ridge 105 with the cap retention groove 110 removably secures the cap 100 to the catheter hub 60.

Other cap retention techniques may be employed with other catheter device embodiments. Other exemplary catheter device embodiments may or may not include a cap.

Other exemplary catheter device embodiments also may utilize catheter portion position retaining mechanisms that differ from the particular detent mechanism shown in FIGS. 1D and 2D and described above. One exemplary embodiment of such an alternative position retention mechanism is depicted in FIGS. 4A-4D.

The exemplary arteriovenous catheter device 200 depicted in FIGS. 4A-4D again includes a body 205 and a catheter portion 225 that are supported on a needle portion 210. The design and interrelationship of each of the needle portion 205 and the catheter portion 225 is generally as described above, as is the basic concept of using the device 200 in a hemodialysis operation. Thus, the needle portion 210 again includes a needle hub 215 and a needle 220. Likewise, the catheter portion 225 again includes a catheter hub 230 and a catheter 235.

In the case of the exemplary arteriovenous catheter device 200 shown in FIGS. 4A-4D, the catheter portion retention mechanism employs a bolt element 240 having a shaft portion 245 that extends from the needle hub 215 through a detent groove 250 in the catheter hub 230 to limit movement and retain the position of the catheter portion 225 of the device relative to the needle portion 210 of the device. The shaft 245 of the bolt element 240 may include an enlarged end portion 255 to ensure the bolt element shaft 245 and the detent groove 250 in the catheter hub 230 remain engaged.

Figure 4A:
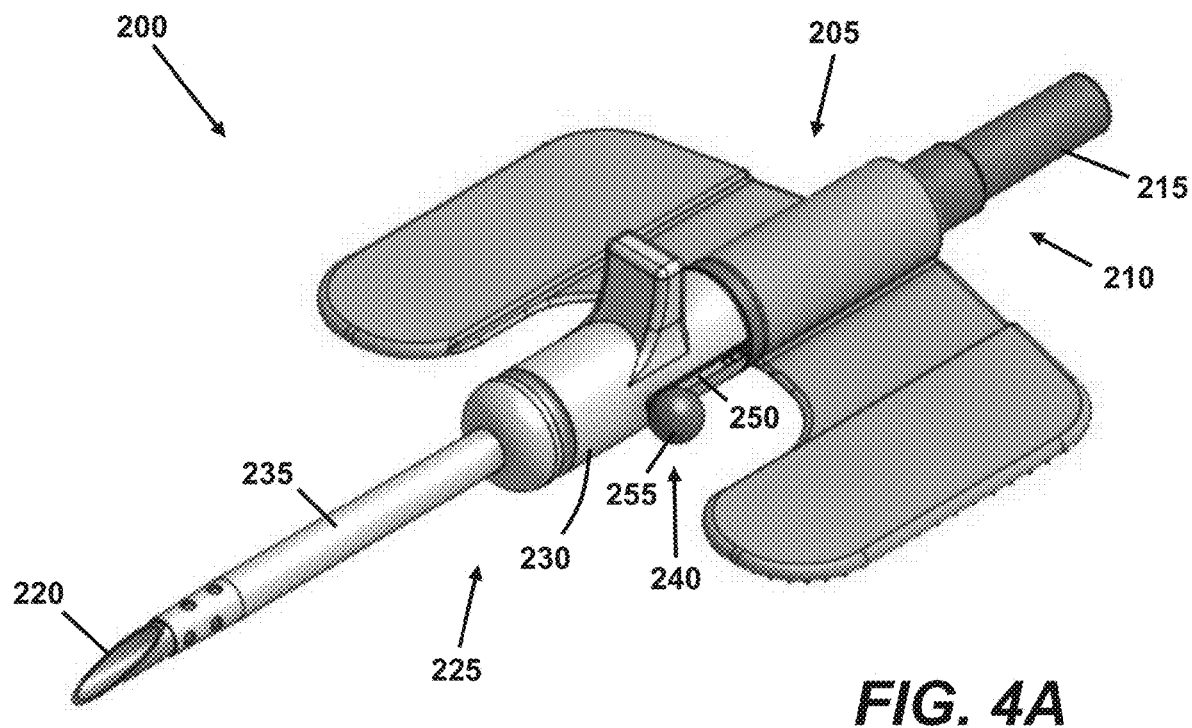
FIGS. 4A-4B are a top perspective view and a side view, respectively, of another exemplary embodiment of a catheter device according to the general inventive concept, with a catheter portion thereof in a retracted position to expose a needle tip.
Figure 4B:
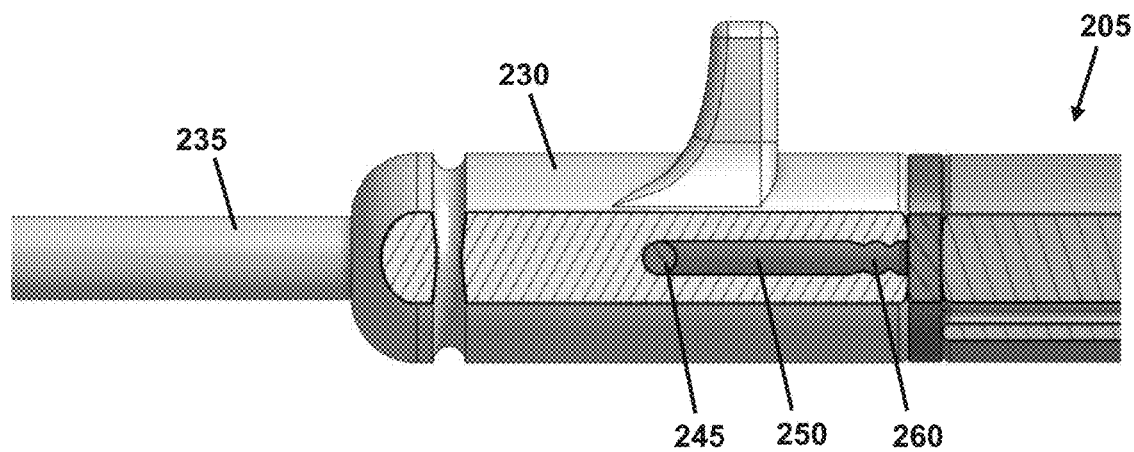
Figure 4C:
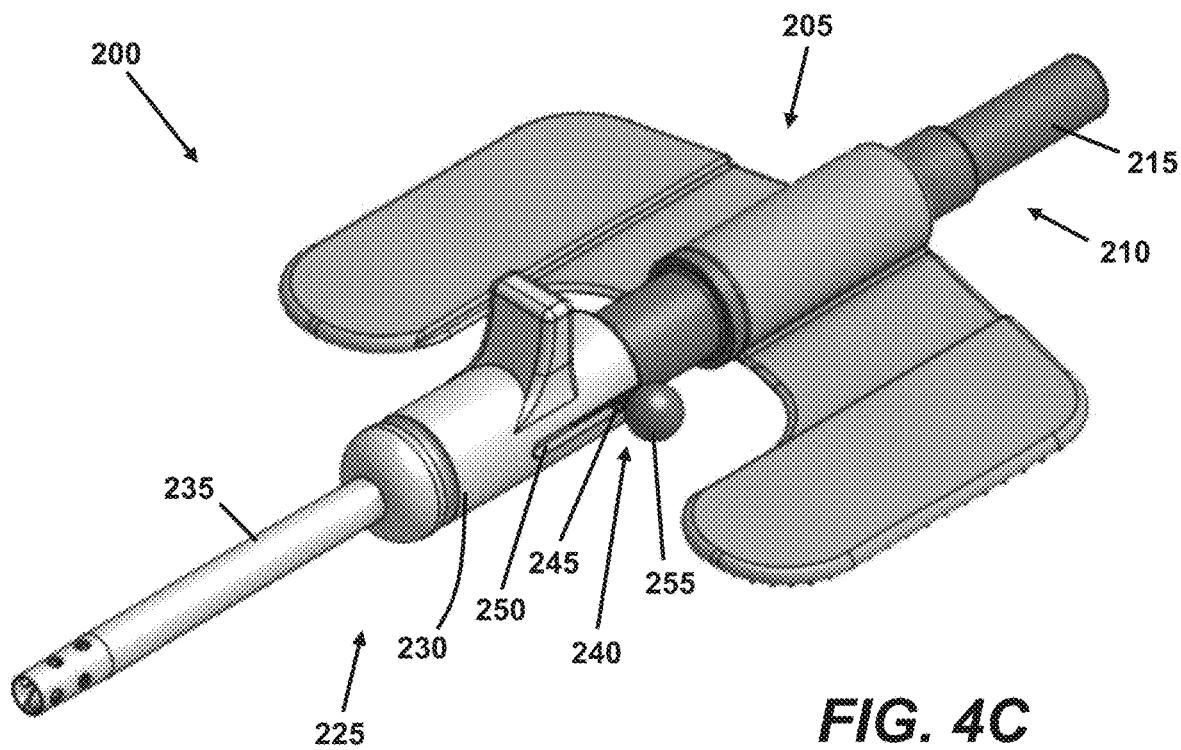
FIGS. 4C-4D are a top perspective view and a side view, respectively, showing the catheter device of FIGS. 4A-4B with the catheter portion thereof in an extended position to cover the needle tip.
Figure 4D:
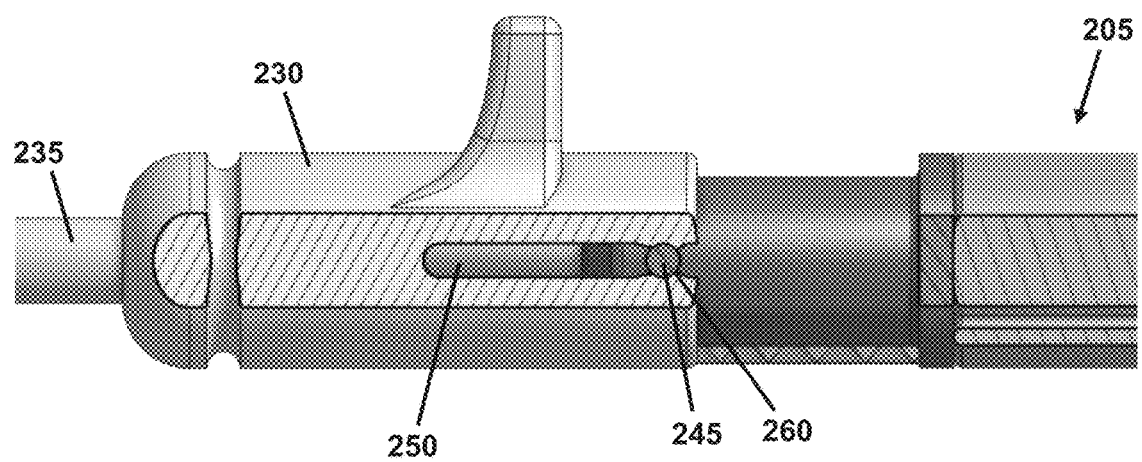

As shown most clearly in FIG. 4B, the detent groove 250 may be configured such that the shaft 245 of the bolt element 240 is in contact with the closed end of the detent groove 250 when the catheter portion 225 is in a retracted position. Referring also to FIG. 4D, it can be further observed that the detent groove 250 may include one or more detent notches 260 that are releasably engageable with the shaft 245 of the bolt element 240 when the catheter portion 225 is in an extended position. The interaction between the detent notches 260 and the shaft 245 of the bolt element 240 serves to retain the catheter portion 225 in the extended position unless an overcoming displacement force is provided by the user.

Another exemplary embodiment of an alternative catheter portion position retention mechanism is depicted in FIGS. 5A-5D. The exemplary arteriovenous catheter device 300 depicted in FIGS. 5A-5D again includes a body 305 and a catheter portion 325 that are supported on a needle portion 310. The design and interrelationship of each of the needle portion 305 and the catheter portion 325 is generally as described above, as is the basic concept of using the device 300 in a hemodialysis operation. Thus, the needle portion 310 again includes a needle hub 315 and a needle 320. Likewise, the catheter portion 325 again includes a catheter hub 330 and a catheter 335.

In the case of the exemplary arteriovenous catheter device 300 shown in FIGS. 5A-5D, the catheter portion retention mechanism employs a tab 340 that extends from the catheter hub 325 into a detent groove 345 in the needle hub 315 to limit movement and retain the position of the catheter portion 325 of the device relative to the needle portion 310 of the device. The tab 340 may be provided, for example, in the form of a pin.

Figure 5A:
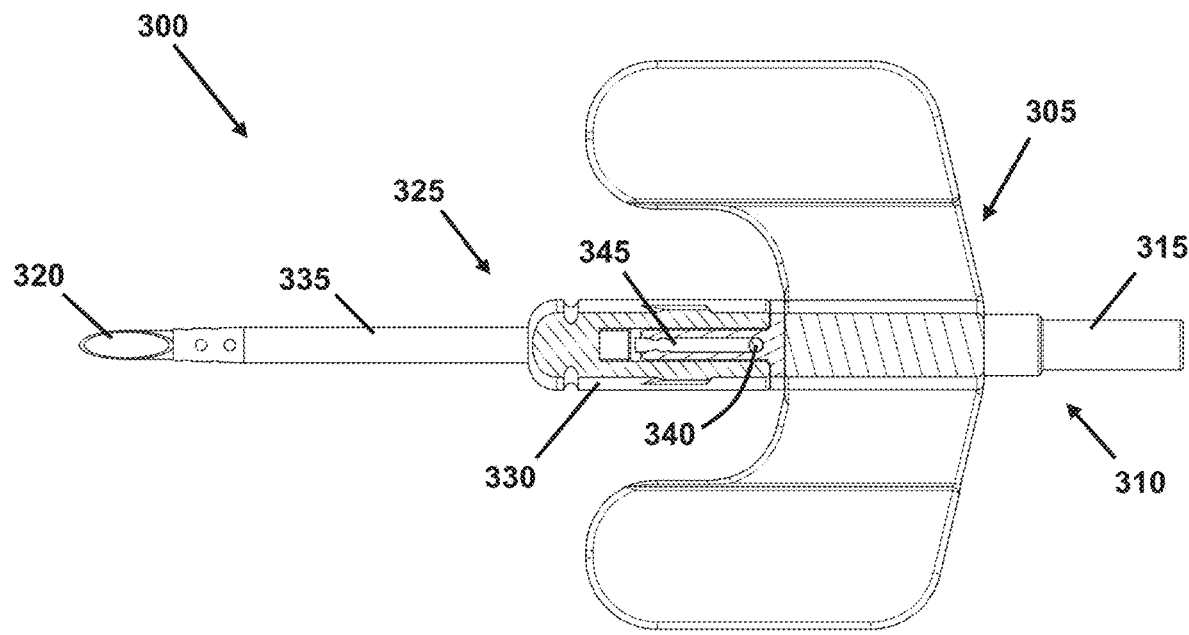
FIG. 5A is a top perspective view of another exemplary embodiment of a catheter device according to the general inventive concept, with a catheter portion thereof in a retracted position to expose a needle tip.
Figure 5B:
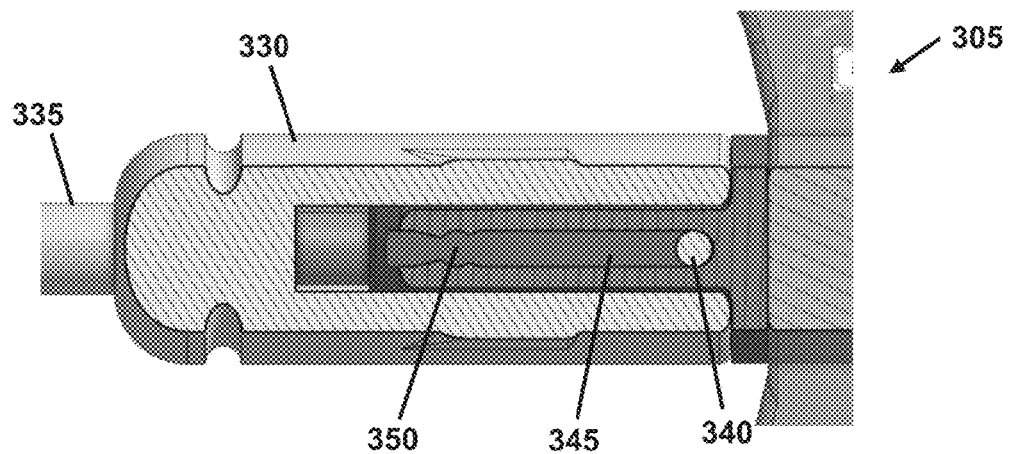
FIG. 5B is an enlarged top plan and partial section view of a portion of the catheter device of FIG. 5A.
Figure 5C:
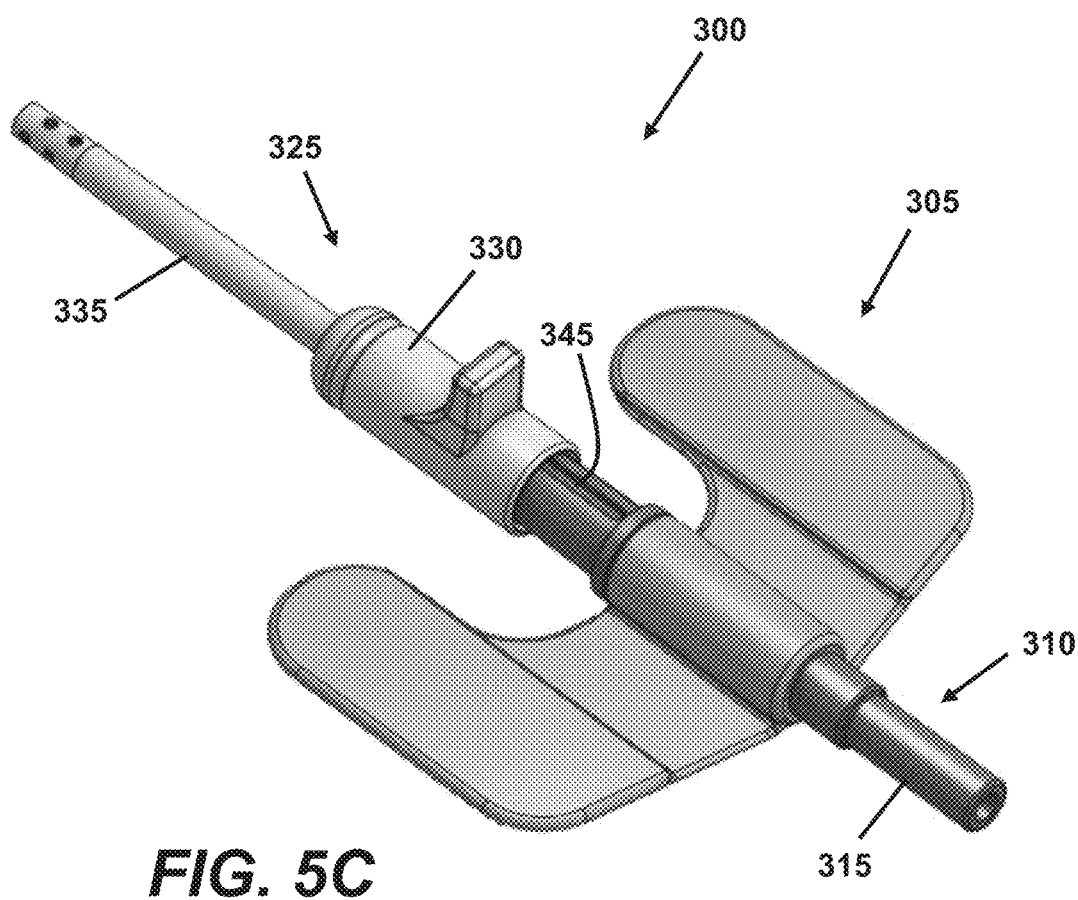
FIG. 5C shows the catheter device of FIG. 5A with the catheter portion in an extended position to cover the needle tip.
Figure 5D:
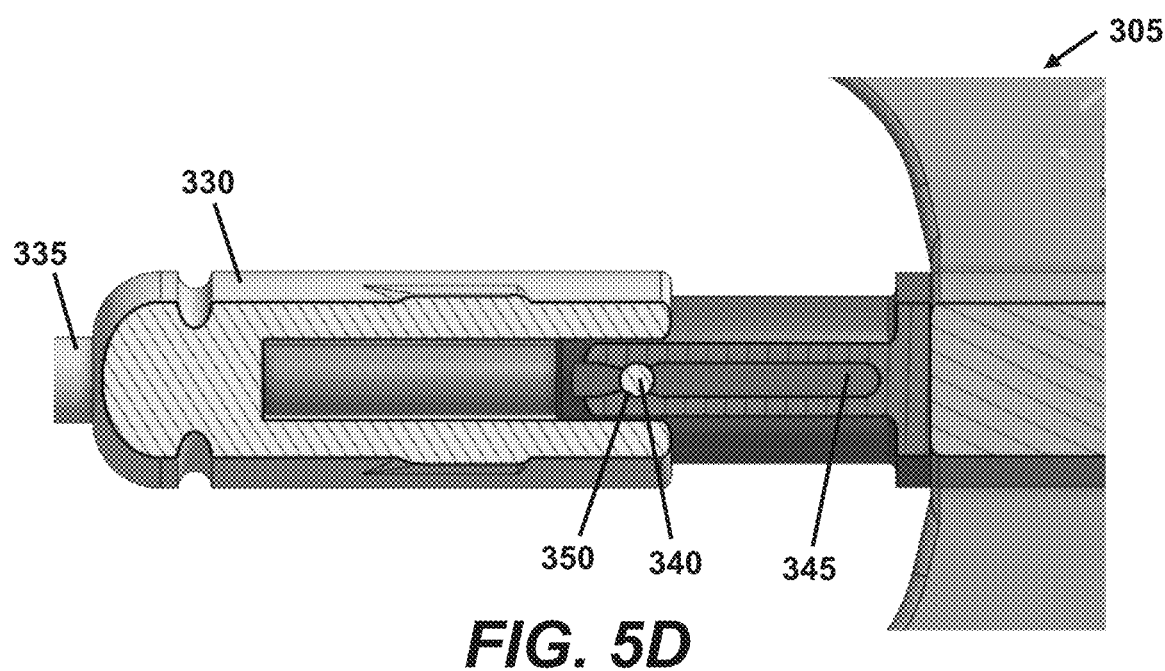
FIG. 5D is an enlarged top plan and partial section view of a portion of the catheter device of FIG. 5C.

As shown most clearly in FIG. 5B, the detent groove 345 may be configured such that the tab 340 is in contact with the closed end of the detent groove 345 when the catheter portion 325 is in a retracted position. Referring to FIG. 5D, it can also be observed that the detent groove 345 may include one or more detent notches 350 that are releasably engageable with the tab 340 when the catheter portion 325 is in an extended position. The interaction between the detent notches 350 and the tab 340 serves to retain the catheter portion 325 in the extended position unless an overcoming displacement force is provided by the user.

Figure 6A:
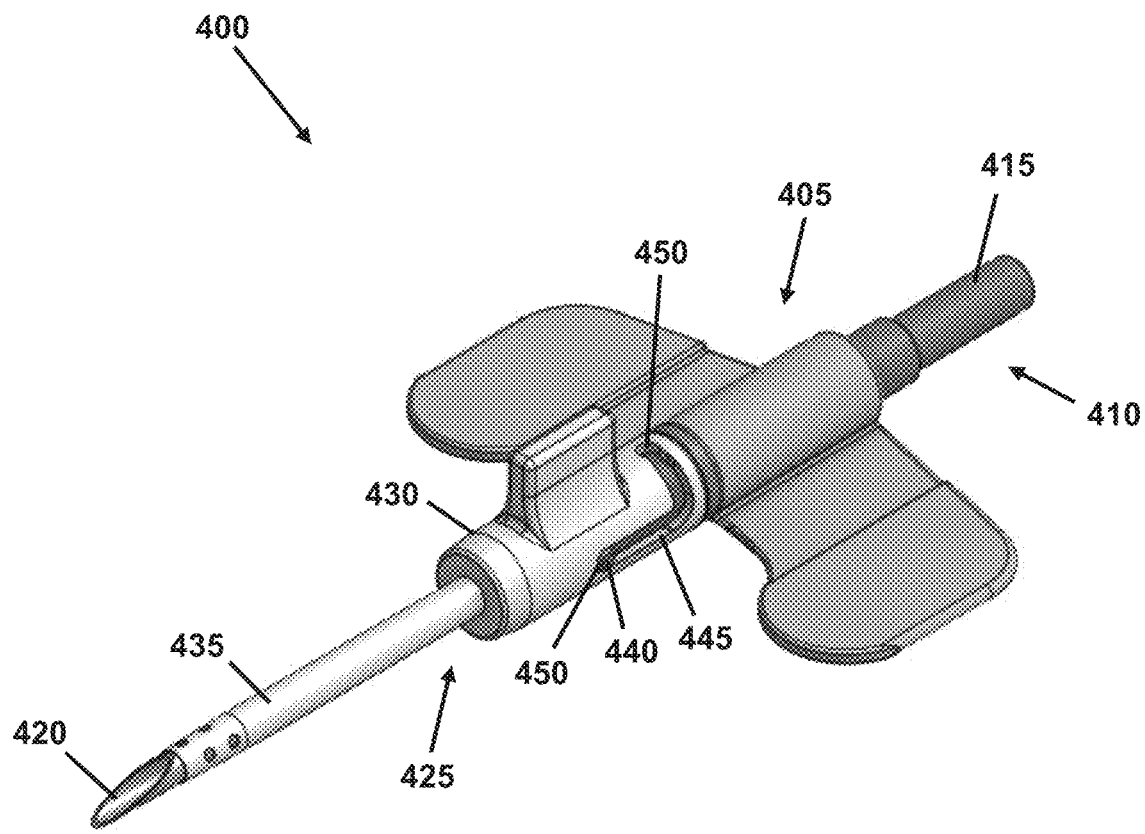
FIG. 6A is a top perspective view of another exemplary embodiment of a catheter device according to the general inventive concept, with a catheter portion thereof in a retracted position to expose a needle tip.
Figure 6B:
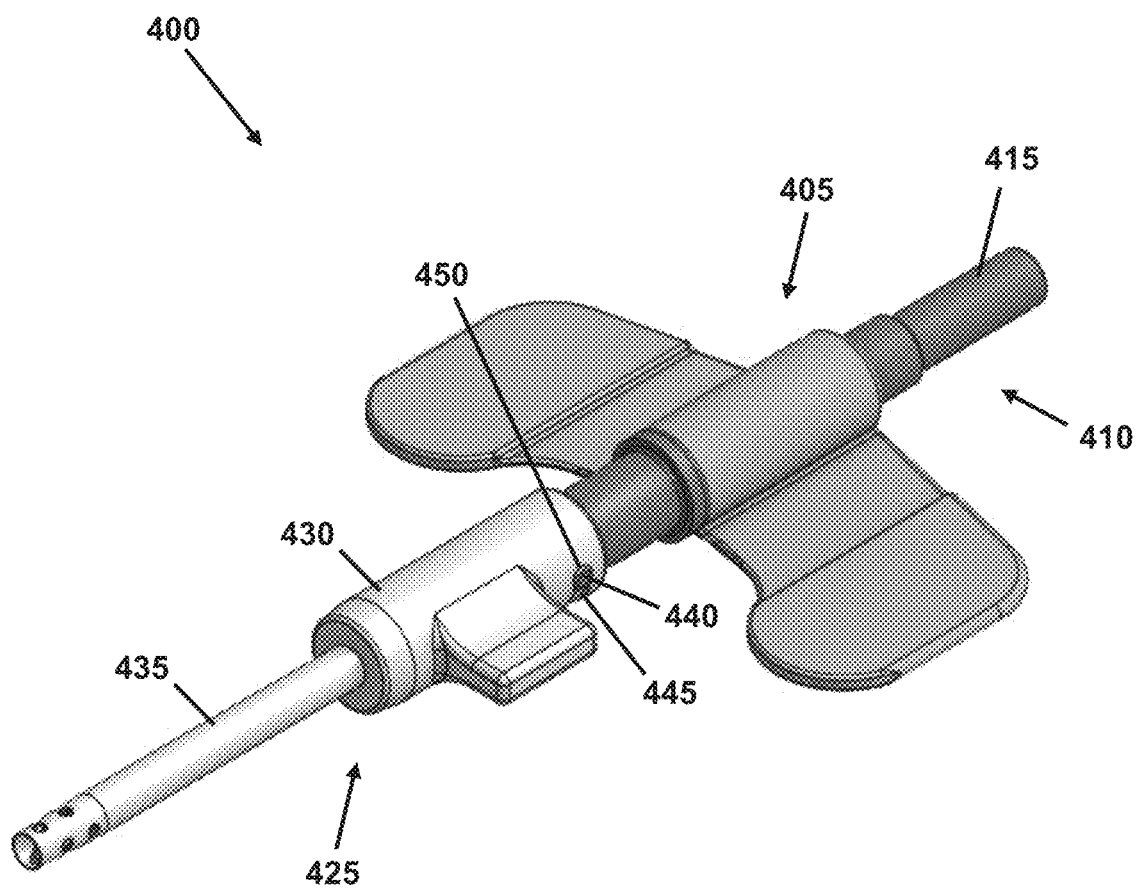
FIG. 6B shows the catheter device of FIG. 6A with the catheter portion in an extended position to cover the needle tip.

Another exemplary embodiment of an alternative catheter portion position retention mechanism is depicted in FIGS. 6A-6B. The exemplary arteriovenous catheter device 400 depicted in FIGS. 6A-6B again includes a body 405 and a catheter portion 425 that are supported on a needle portion 410. The design and interrelationship of each of the needle portion 410 and the catheter portion 425 is generally as described above, as is the basic concept of using the device 400 in a hemodialysis operation. Thus, the needle portion 410 again includes a needle hub 415 and a needle 420. Likewise, the catheter portion 425 again includes a catheter hub 430 and a catheter 435.

In the case of the exemplary arteriovenous catheter device 400 shown in FIGS. 6A-6B, the catheter portion retention mechanism employs a pin 440 that extends from the needle hub 415 through a curved cam slot 445 in the catheter hub 430 to limit movement and retain the position of the catheter portion 425 of the device relative to the needle portion 410 of the device. The cam slot 445 may be configured so as to wrap at least partially around the circumference of the catheter hub 430. As such, a linear displacement of the catheter hub 430 along the needle hub 415 will also produce a rotation of the catheter portion. During use of this exemplary arteriovenous catheter device 400, the cam slot 445 allows for parking of the catheter portion 425 in an extended position before final engagement, which permits minor adjustments to the catheter 435 and the needle 420 to obtain optimum blood flow.

The pin 440 may be in contact with a distal end of the cam slot 445 when the catheter portion 425 is in a retracted position. The pin 440 may be in contact with a proximal end of the cam slot 445 when the catheter portion 425 is in an extended position. The cam slot 445 may include one or more detent notches 450 at each end thereof that are respectively releasably engageable with the pin 440 when the catheter portion 425 is in an extended or retracted position. The interaction between the detent notches 450 and the pin 440 serves to retain the catheter portion 425 in the extended or retracted position unless an overcoming displacement force is provided by the user.

Various exemplary embodiments have been described and shown herein for purposes of illustration. Other variations are also possible. For example, and without limitation, the catheter hub and needle hub of an exemplary arteriovenous catheter device, may be manufactured from a transparent or semi-transparent material to permit viewing of the flow of blood passing through the device during use.

Therefore, while certain embodiments of the inventive concept are described in detail above, the scope of the inventive concept is not considered limited by such disclosure, and modifications are possible without departing from the spirit of the inventive concept as evidenced by the following claims:

What is claimed is:

1. An arteriovenous catheter device with an inline needle, comprising:
   a needle portion having an elongate and hollow needle hub and a hollow needle that extends from a distal end of the needle hub;
   a catheter portion having a hollow catheter hub and a hollow catheter that extends from a distal end of the catheter hub, the catheter hub supported on the needle hub with at least a portion of the needle located in the catheter; and
   a gripping portion coupled to the needle hub and configured to facilitate manipulation of the device by a user;
   wherein the needle portion is permanently coupled to the catheter portion but the catheter portion is selectively linearly displaceable along the needle portion between a retracted, insertion position where at least a tip of the needle protrudes from the catheter, and an extended, blood transfer position where the needle is covered by the catheter.

2. The arteriovenous catheter device of claim 1, wherein a distal end of the needle hub is configured to receive a proximal end of the needle, and a proximal end of the needle hub is configured for the connection of blood transfer tubing.

3. The arteriovenous catheter device of claim 1, further comprising a stop element that sets the extended position of the catheter portion.

4. The arteriovenous catheter device of claim 1 further comprising a stop element that sets the retracted position of the catheter portion.

5. The arteriovenous catheter device of claim 1, wherein the body includes:
   a substantially hollow central mounting sleeve that is dimensioned to slide over a corresponding portion of the needle hub; and
   combination gripping and device securing elements that extend laterally outward from substantially opposite sides of the central mounting sleeve.

6. The arteriovenous catheter device of claim 1, wherein the distal end of the needle hub is substantially concentrically arranged within the catheter hub, and the needle is substantially concentrically arranged within the catheter.

7. The arteriovenous catheter device of claim 1, further comprising a cap that is removably attachable to the catheter hub and configured to cover the needle and catheter when so attached.

8. The arteriovenous catheter device of claim 1, further comprising a catheter hub positional retention mechanism that is configured to releasably retain the catheter portion in at least the extended position relative to the needle portion.

9. The arteriovenous catheter device of claim 8, wherein the catheter hub positional retention mechanism is a detent mechanism that includes:
   an inwardly-directed annular projection near the open proximal end of the catheter hub; and
   a cooperating annular groove near the distal end of the needle hub;
   wherein the projection and groove are located and configured such that the projection will releasably engage the groove when the catheter portion is placed in the extended position.

10. The arteriovenous catheter device of claim 8, wherein the catheter hub positional retention mechanism is a detent mechanism that is selected from the group consisting of a pin or shaft that extends outward from the needle hub and into a detented slot in the catheter hub; a detent mechanism that includes a pin or shaft that extends inward from the catheter hub and into a detented slot in the needle hub; and a pin or bolt that extends outward from the needle hub and into a cam slot in the catheter hub, the cam slot having both a longitudinally oriented and circumferentially oriented segment.

11. The arteriovenous catheter device of claim 10, further comprising a detent in at least one end of the cam slot.

12. The arteriovenous catheter device of claim 10, wherein interaction between the pin or bolt and the cam slot allows for parking of the catheter portion in the extended position before final engagement with a patient.

13. The arteriovenous catheter device of claim 1, further comprising a seal located between an outside surface of the needle and an inside surface of the catheter for preventing blood leakage therebetween.

14. The arteriovenous catheter device of claim 1 wherein the fit between an outside surface of the needle and an inside surface of the catheter forms a seal sufficient to prevent blood leakage therebetween.

15. The arteriovenous catheter device of claim 1, further comprising:
blood transfer tubing connected at a first end to an open proximal end of the needle hub and at an opposite end to a dialysis machine;
whereby the catheter and needle are insertable into the bloodstream of a patient without a break in the overall dialysis blood flow path.

16. An arteriovenous catheter device with an inline needle, comprising:
a needle portion having an elongate hollow needle hub with a proximal end that is configured for the connection of blood transfer tubing, and a hollow needle that extends longitudinally outward from a distal end of the needle hub and includes a distal tip;
a catheter portion having a hollow catheter hub, and a hollow catheter that extends axially outward from a distal end of the catheter hub, the catheter hub supported on the needle hub such that at least a portion of the needle resides within the catheter, the catheter portion irremovably coupled to the needle portion but selectively linearly displaceable along the needle portion between a retracted, insertion position where at least a tip of the needle protrudes from the catheter, and an extended, blood transfer position where the catheter covers the needle;
a catheter portion positional retention mechanism; and
a gripping portion coupled to the needle hub and configured to facilitate manipulation of the device by a user.

17. The arteriovenous catheter device of claim 16, further comprising a stop element that sets the retracted position of the catheter portion.

18. The arteriovenous catheter device of claim 16, wherein the catheter hub retention mechanism includes a pin or bolt that extends outward from the needle hub and into a cam slot in the catheter hub, the cam slot having both a longitudinally oriented and circumferentially oriented segment and a detent in at least one end.

19. The arteriovenous catheter device of claim 16, further comprising:
blood transfer tubing connected at a first end to the proximal end of the needle hub and at an opposite end to a hemodialysis machine;
whereby the catheter and needle are insertable into the bloodstream of a patient without a break in the overall dialysis blood flow path.

20. The arteriovenous catheter device of claim 16, further comprising a stop element that sets the extended position of the catheter portion.

21. An arteriovenous catheter assembly for hemodialysis treatment, comprising:
an arteriovenous catheter device, further comprising:
a needle portion having an elongate hollow needle hub, and a hollow needle that extends longitudinally outward from a distal end of the needle hub and includes a distal tip;
a catheter portion having a hollow catheter hub and a hollow catheter that extends axially outward from a distal end of the catheter hub, the catheter hub supported on the needle hub such that at least a portion of the needle resides within the catheter, the catheter portion irremovably coupled to the needle portion but selectively linearly displaceable along the needle portion between a retracted, insertion position where at least a tip of the needle protrudes from the catheter, and an extended, blood transfer position where the needle is covered by the catheter;
a catheter portion positional retention mechanism; and
a gripping portion coupled to the needle hub and configured to facilitate manipulation and securing of the device by a user; and
a length of blood transfer tubing connected at a first end to a proximal end of the needle hub and at a second end to a hemodialysis machine;
wherein, the catheter and needle are insertable into the bloodstream of a patient and the arteriovenous catheter device is thereafter useable to transfer blood from/to the patient without a break in an overall blood flow path between the patient and the hemodialysis machine.

22. The assembly of claim 21, further comprising at least one stop element by which the extended and retracted positions of the catheter portion are set.

* * * * *